(12) United States Patent
Cropper

(10) Patent No.: US 8,926,539 B2
(45) Date of Patent: Jan. 6, 2015

(54) KNEE ORTHOSIS AND ORTHOTIC METHOD

(76) Inventor: Dean E. Cropper, Ashland, OR (US)

(*) Notice: Subject to any disclaimer, the term of this patent is extended or adjusted under 35 U.S.C. 154(b) by 0 days.

(21) Appl. No.: 10/796,171

(22) Filed: Mar. 10, 2004

(65) Prior Publication Data

US 2005/0203455 A1    Sep. 15, 2005

(51) Int. Cl.
*A61F 5/00* (2006.01)
*A61F 5/01* (2006.01)

(52) U.S. Cl.
CPC ....... *A61F 5/0123* (2013.01); *A61F 2005/0176* (2013.01)
USPC .................................. 602/26; 602/23; 602/62

(58) Field of Classification Search
USPC ............. 602/16, 26, 62, 23, 60, 61, 63, 5, 28; 128/882, 892
See application file for complete search history.

(56) References Cited

U.S. PATENT DOCUMENTS

| | | | |
|---|---|---|---|
| 2,188,718 A | | 1/1940 | Jung |
| 2,476,565 A | | 7/1949 | Russell |
| 2,858,540 A | * | 11/1958 | Morrison ............................ 2/24 |
| 3,463,147 A | | 8/1969 | Stubbs |
| 3,804,084 A | * | 4/1974 | Lehman .......................... 602/26 |
| 3,934,583 A | | 1/1976 | Hollingshead |
| 4,084,584 A | | 4/1978 | Detty |
| 4,120,052 A | | 10/1978 | Butler |
| 4,201,203 A | * | 5/1980 | Applegate ....................... 602/26 |
| 4,296,744 A | * | 10/1981 | Palumbo ......................... 602/26 |
| 4,334,528 A | | 6/1982 | Gauvry |
| 4,353,362 A | | 10/1982 | DeMarco |
| 4,370,978 A | * | 2/1983 | Palumbo ......................... 602/26 |
| 4,445,505 A | * | 5/1984 | Labour et al. ................... 602/26 |
| 4,474,573 A | | 10/1984 | Detty |
| 4,520,802 A | | 6/1985 | Mercer et al. |
| 4,532,921 A | * | 8/1985 | von Torklus et al. ........... 602/26 |
| 4,572,170 A | * | 2/1986 | Cronk et al. .................... 602/26 |
| 4,607,628 A | * | 8/1986 | Dashefsky ....................... 602/26 |
| 4,700,698 A | | 10/1987 | Kleylein |
| 4,765,318 A | | 8/1988 | Tranberg et al. |
| 4,777,946 A | * | 10/1988 | Watanabe et al. ............... 602/62 |
| 4,781,179 A | * | 11/1988 | Colbert ........................... 602/16 |
| D307,054 S | * | 4/1990 | Johnson, Jr. |

(Continued)

OTHER PUBLICATIONS

Powers et al., "The Effect of Bracing on Patellofemoral Joint Stress During Free and Fast Walking". The Am. J. of Sports Med., vol. 32, No. 1, (publication Feb. 2004).*

(Continued)

*Primary Examiner* — Victoria J Hicks
*Assistant Examiner* — Keri J Nelson
(74) *Attorney, Agent, or Firm* — Durham Jones & Pinegar Intellectual Property Law Group

(57) ABSTRACT

A knee orthosis that includes a medial tracking member that operatively fits along a lateral side of, and provides medial traction to, a patella having patellofemoral articular tissue; an inward tracking member that operatively fits over, and provides inward pressure against, the patella; wherein the inward tracking member provides a compressive force against the patella, thereby increasing the contact surface area between the patellofemoral articular tissue and an associated femoral trochlear groove. The inward tracking member overlays the patella and the medial tracking member so that medial traction can be placed on the patella. The inward tracking member provides continued compressive force against the patella to stretch lateral connective tissue of the patella, throughout a full extension or flexion motion of an associated knee, and the continuous compressive force is substantially the same throughout the extension or flexion motion. An orthotic method for correcting patellofemoral joint disorders is also disclosed.

25 Claims, 3 Drawing Sheets

(56) References Cited

U.S. PATENT DOCUMENTS

| | | | |
|---|---|---|---|
| 4,915,098 A | | 4/1990 | Young et al. |
| 5,005,565 A | | 4/1991 | Fratesi |
| 5,016,621 A | * | 5/1991 | Bender .................. 602/26 |
| 5,024,216 A | * | 6/1991 | Shiono .................. 602/26 |
| 5,038,765 A | | 8/1991 | Young et al. |
| 5,135,469 A | | 8/1992 | Castillo |
| 5,221,252 A | | 6/1993 | Caprio, Jr. et al. |
| 5,277,697 A | * | 1/1994 | France et al. .......... 602/16 |
| 5,407,421 A | | 4/1995 | Goldsmith |
| 5,411,037 A | | 5/1995 | Hess et al. |
| 5,417,646 A | * | 5/1995 | Gauvry .................. 602/26 |
| 5,474,524 A | | 12/1995 | Carey |
| 5,554,105 A | | 9/1996 | Taylor |
| 5,556,374 A | | 9/1996 | Grace et al. |
| 5,584,802 A | | 12/1996 | Hess et al. |
| 5,586,970 A | * | 12/1996 | Morris et al. .......... 602/26 |
| 5,613,943 A | | 3/1997 | Palumbo |
| 5,649,901 A | | 7/1997 | DiPietro |
| 5,656,023 A | | 8/1997 | Caprio, Jr. et al. |
| 5,735,807 A | | 4/1998 | Cropper |
| 5,743,866 A | * | 4/1998 | Bauerfeind et al. .... 602/63 |
| 5,759,167 A | * | 6/1998 | Shields et al. ......... 602/26 |
| 5,800,491 A | * | 9/1998 | Kolen et al. ........... 607/108 |
| 5,807,298 A | | 9/1998 | Palumbo |
| 5,814,002 A | | 9/1998 | Nelson |
| 5,827,208 A | | 10/1998 | Mason |
| 5,865,776 A | | 2/1999 | Springs |
| 5,865,777 A | * | 2/1999 | Detty .................... 602/26 |
| 5,925,010 A | | 7/1999 | Caprio, Jr. et al. |
| 5,944,682 A | | 8/1999 | Milana-Panupoulos |
| 6,013,039 A | | 1/2000 | Watkins et al. |
| 6,059,743 A | * | 5/2000 | Reinhardt et al. ..... 602/26 |
| 6,074,355 A | | 6/2000 | Bartlett |
| 6,077,242 A | * | 6/2000 | Falk et al. ............. 602/62 |
| 6,080,124 A | | 6/2000 | Falk et al. |
| 6,149,616 A | | 11/2000 | Szlema et al. |
| 6,152,893 A | * | 11/2000 | Pigg et al. ............. 602/75 |
| 6,168,569 B1 | | 1/2001 | McEwen et al. |
| 6,238,360 B1 | * | 5/2001 | Gildersleeve et al. .. 602/26 |
| 6,287,269 B1 | * | 9/2001 | Osti et al. ............. 602/62 |
| 6,311,334 B1 | | 11/2001 | Reinhardt |
| 6,336,909 B2 | | 1/2002 | Gildersleeve et al. |
| 6,485,448 B2 | * | 11/2002 | Lamping et al. ....... 602/26 |
| 6,520,926 B2 | | 2/2003 | Hall |
| 6,551,264 B1 | * | 4/2003 | Cawley et al. ......... 602/16 |
| 6,592,539 B1 | | 7/2003 | Einarsson et al. |
| 6,641,549 B2 | * | 11/2003 | Darcey ................. 602/8 |
| 6,790,192 B2 | | 9/2004 | Robinson |
| 6,852,088 B2 | | 2/2005 | Gaylord |
| 6,863,657 B1 | * | 3/2005 | Clements et al. ...... 602/26 |
| 6,974,433 B2 | | 12/2005 | Hess |
| 6,994,682 B2 | | 2/2006 | Bauerfiend et al. |
| 7,004,919 B2 | * | 2/2006 | Gaylord et al. ........ 602/62 |
| 7,011,641 B1 | * | 3/2006 | DeToro et al. ........ 602/26 |
| 2001/0014782 A1 | | 8/2001 | Gildersleeve et al. |
| 2002/0052568 A1 | | 5/2002 | Houser et al. |
| 2002/0077574 A1 | | 6/2002 | Gildersleeve |
| 2002/0147422 A1 | | 10/2002 | Darcey et al. |
| 2002/0165475 A1 | | 11/2002 | Chiang et al. |
| 2003/0187375 A1 | * | 10/2003 | Gaylord ................ 602/26 |
| 2003/0204156 A1 | | 10/2003 | Nelson et al. |
| 2004/0054307 A1 | * | 3/2004 | Mason et al. ......... 602/16 |
| 2004/0153017 A1 | * | 8/2004 | Simmons et al. ...... 602/26 |

OTHER PUBLICATIONS

Kay Cerny, Vastus Medialis Oblique/Vastus Lateralis Muscle Activity Ratios for Selected [ . . . ], Physical Therapy, Aug. 1995, pp. 672-683, vol. 75, No. 8, USA.

P.M. Palumbo, Dynamic patellar brace: A new orthosis [ . . . ], Am. J. Sports Med., 1981, pp. 45-49, vol. 9; No. 45, Am. Ortho. Soc. for Spor. Med., USA.

Charles Milgram et al., Treatment of Overuse Patellofemoral Pain [ . . . ], Clinical Orthopedicis and Related Research, 1993, pp. 208-210, No. 293, J.B. Lippincott Co., USA.

Christopher M. Powers, Ph.D., PT, Rehabilitation of Patellofemoral Joint Disorders: A Crit[ . . . ], Jour. Ortho. & Sports Phy. Ther., Nov. 1998, pp. 345-354, vol. 28, No. 5, USA.

Jenny McConnell et al., Effects of taping on patella position[ . . . ], Med. Sci. Sports. Exerc., Sep. 1993, pp 989-992, vol. 25, No. 9, Lippincott Williams, USA.

Wendy Gilleard et al., The effect of patellar taping[ . . . ], Phys. Ther., Jan. 1998, pp. 25-32, vol. 78, No. 1, USA.

Frank Shellock et al., Effect of a newly designed patellar realignment brace[ . . . ], Med. & Sci. in Spor. & Exerc., 1995, pp. 469-472, Amer. Col. Spor. Med., USA.

B.N. Moller et al., Dynamic knee brace in the treatment of patellofemoral [ . . . ], Arch. Orthop. Trauma Sur., 1986, pp. 377-379, vol. 104, Denmark.

* cited by examiner

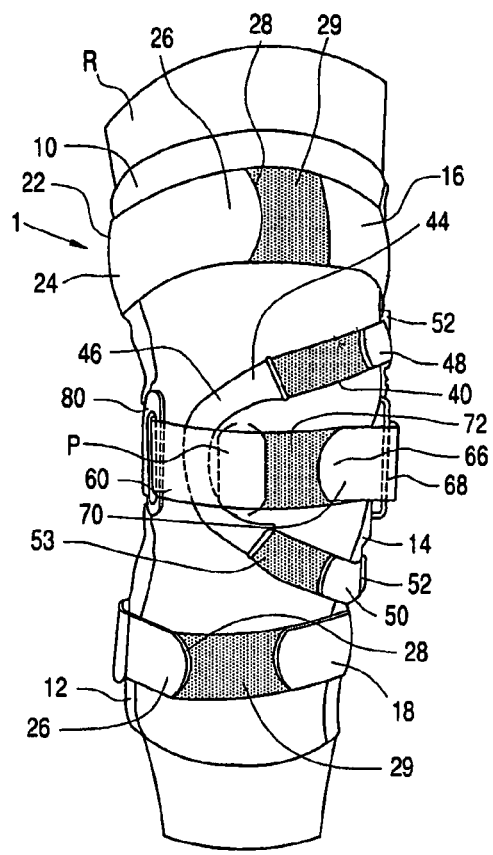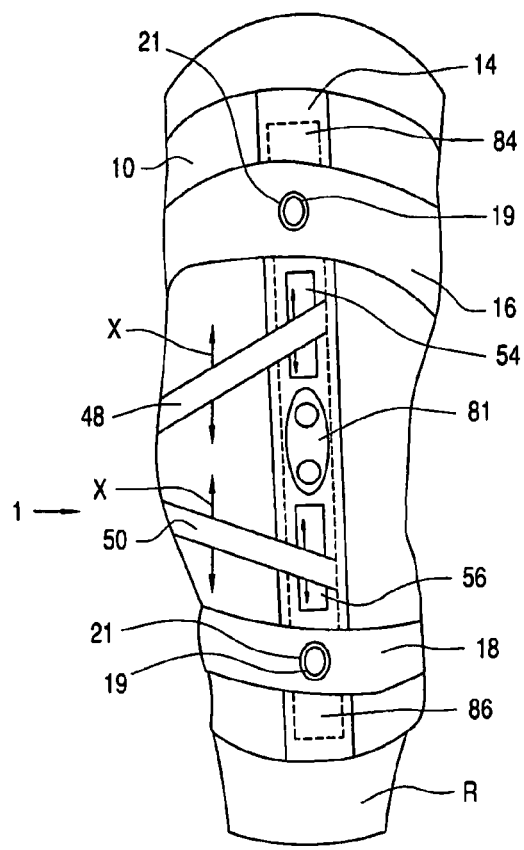
FIG. 1  FIG. 1a
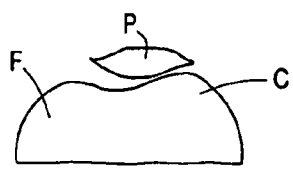
FIG. 2a
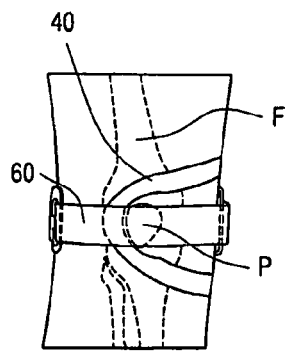
FIG. 2b
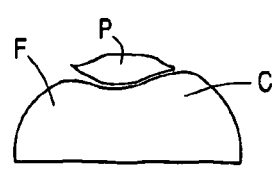
FIG. 2c

KNEE ORTHOSIS AND ORTHOTIC METHOD

FIELD OF THE INVENTION

The present invention relates to a knee orthosis and an orthotic method. More particularly, the present invention relates to a knee orthosis and an orthotic method that creates medial traction forces in the patellofemoral joint to reduce pain, increase function and speed rehabilitation.

BACKGROUND OF THE INVENTION

The patellofemoral joint of the knee is an articulating joint between the patella and the femur. More specifically, this joint consists of an articular surface on the posterior of the patella and a corresponding articular surface on the anterior distal portion of the femur, also termed the trochlear groove. The posterior of the patella is contoured as a ridge, while the trochlea is contoured as a groove that is dimensioned to receive the patellar ridge in a complementary manner. Proper dynamic function of the patellofemoral joint requires that the patellar ridge accurately track the underlying trochlear groove when the knee is moved through flexion or extension.

Joint disorders nevertheless arise with varying severity, pain and dysfunction. Some less severe, albeit still painful, disorders involve minimal or no errors in patellar tracking of the trochlear groove. Other more serious disorders are characterized by patellar subluxation, i.e., transient displacement, or dislocation, i.e., permanent displacement, of the patella from the trochlear groove.

Most frequently, such tracking errors occur in the lateral direction and therefore require corrective medial traction. During functional movement of the knee joint, that is—typically from 0° to 60° of knee flexion, lateral tracking can occur due to injury, overuse, or changes inherent to adolescent growth, which in each of these cases causes pain and dysfunction. When the patella is seated in the trochlear groove at a range greater than about 60° of knee flexion, there is very little movement of the patella outside of the trochlear groove. Between about 0° and 40° of knee flexion, and especially about 20° to 40°, however, there is a propensity for the patella to track laterally as the knee flexes. As a result, effective medial traction forces must be applied in conjunction with exercise to direct the patella for improved tracking.

Rehabilitation of the weakened joint is therefore limited to the extent that true medial traction is absent, or ineffectively applied. While some devices may stabilize the patella, they fail to provide consistent, continuous traction force, and therefore fail to affect proper patellar tracking. It is important, moreover, to provide medial traction (and not mere stabilization) throughout a full range of knee flexion and extension motion.

In addition, biomechanical forces typically bias the patella laterally when the knee is load bearing. During knee extension, the quadriceps contract to exert a lever force about the patellofemoral joint, whereby the patella is pulled up along the trochlear groove. As the patella moves up the trochlear groove, the trochlear groove narrows, thereby forcing the patella to project more outwardly. Nearly simultaneous application of load bearing pressure may result in either momentary or permanent lateral displacement of the patella such that medial traction must be used to correct or prevent the prevailing lateral subluxation or dislocation.

As the quadriceps contract, they apply a lever force to the patellofemoral joint that is, more or less, directly related to the overall patellofemoral joint stress. Pain associated with such stress increases in relation to the amount of overall stress. Accordingly, as the quadriceps contract more powerfully, such as while going up stairs or doing squats, overall stress and associated pain increases.

However, patellofemoral joint stress at any given contact area decreases as the overall patellofemoral joint stress is distributed about a greater patellofemoral contact surface area. Pain associated with such stress decreases in inverse relation to the amount of patella-to-femur contact surface area. Thus, patellofemoral pain is not only directly related to the overall joint force applied between the patella and the femur; it is inversely related to the amount of patellofemoral contact surface area. Rehabilitation of the weakened joint through quadriceps contraction is therefore limited by the pain associated with both overall patellofemoral joint stress and a minimal patellofemoral contact surface area.

Because subluxation frequently occurs even early on in the extensor motion, it is moreover important to account for the damage and pain caused by both overall joint stress and a minimal patellofemoral contact surface area, throughout a full range of knee flexion and extension motion.

Prior attempts to provide patellofemoral support fail to provide continuous medial tracking or account for patellofemoral contact surface area as a factor in joint stress. For example, U.S. Pat. No. 6,287,269 B1, entitled "Dynamic Orthesis Device for the Conservative Treatment of Patellofemoral Instability of the Knee", discloses a support element that provides medial tracking of the patella. Continued medial traction is absent, however, and it does not account for damage and pain caused by minimal patellofemoral contact surface area, however.

U.S. Pat. Nos. 6,077,242 and 6,080,124, respectively entitled "Patella Strap" and "Patella Strap Method", disclose a strap that directs either superior or inferior, i.e., downward or upward, pressure on a patella. Continued medial traction is absent, however, and it does not account for damage and pain caused by a minimal patellofemoral contact surface area, or provide medial tracking of the patella.

U.S. Pat. No. 6,592,539 B1, entitled "Orthotic or Prosthetic Sleeve Formed of Elasticized Fabric Sections Having Different Elastic Stiffness", discloses a compression sleeve having a section that fits over the entire knee and includes unidirectional stretchable fabric that stretches along the sleeve's axis. It does not, however, account for damage and pain caused by a minimal patellofemoral contact surface area, or provide medial tracking of the patella.

U.S. Pat. No. 4,607,628, entitled "Patella Support Brace", discloses a patella pad that exerts a medial and distal pressure on the patella during knee extension. Continued medial traction is absent, however, and it does not account for damage and pain caused by minimal patellofemoral contact surface area.

U.S. Pat. No. 6,551,264 B1, entitled "Orthosis for Dynamically Stabilizing the Patello-femoral Joint", discloses a knee orthosis having a patellar tracking guide that tensions as the knee extends. It does not, however, account for damage and pain caused by a minimal patellofemoral contact surface area, or provide medial tracking throughout a full range of knee flexion and extension motion.

Hence, the prior art fails to provide a knee brace that provides medial traction and that accounts for pain caused by a minimal patellofemoral contact surface area throughout a full range of flexion and extension motion.

SUMMARY OF THE INVENTION

Thus, the present invention is directed to a knee orthosis that provides continued medial traction of a patella's lateral connective tissue.

The present invention is alternately or additionally directed to a knee orthosis that provides medial traction of a patella's lateral connective tissue throughout a full range of flexion and extension motion.

The present invention is alternately or additionally directed to a knee orthosis that provides direct inward pressure on a patella.

The present invention is alternately or additionally directed to a knee orthosis that provides inward pressure on a patella throughout a full range of flexion and extension motion.

The present invention is alternately or additionally directed to an orthotic method that provides continued medial traction of a patella's lateral connective tissue.

The present invention is alternately or additionally directed to an orthotic method that provides medial traction of a patella's lateral connective tissue throughout a full range of flexion and extension motion.

The present invention is alternately or additionally directed to an orthotic method that provides direct inward pressure on a patella.

The present invention is alternately or additionally directed to an orthotic method that provides inward pressure on a patella throughout a full range of flexion and extension motion.

One aspect of the present invention is directed to a knee orthosis that includes a medial tracking member that operatively fits along a lateral side of, and provides medial traction to, a patella having patellofemoral articular tissue; and an inward tracking member that operatively fits over, and provides inward pressure against, the patella; wherein the inward tracking member provides a compressive force against the patella, thereby increasing the contact surface area between the patellofemoral articular tissue and an associated femoral trochlear groove.

In another aspect, the inward pressure is applied through an intermittent and progressively increased tightening of the inward tracking member.

In yet another aspect, the inward tracking member directly overlays the patella and the medial tracking member so that medial traction can be placed on the patella.

In still another aspect, the medial tracking member is adjustable to increase or decrease an amount of medial traction.

In yet another aspect, the inward tracking member is adjustable to increase or decrease an amount of inward pressure.

In still another aspect, the inward tracking member provides continuous compressive force against the patella throughout a full range of extension motion of an associated knee.

In yet another aspect, the continuous compressive force is substantially the same throughout the extension motion.

In still another aspect, the continuous compressive force increases throughout the extension motion.

In yet another aspect, the knee orthosis comprises a polycentric hinge having an axis that maintains a parallel position with respect to an associated knee throughout a flexion or extension motion of the knee.

In still another aspect, the polycentric hinge is bicentric and the inward tracking member is operatively attached to the hinge and aligned substantially perpendicular to the hinge axis.

In yet another aspect, the inward tracking member is mounted on the hinge, or operatively loops through a ring that is aligned parallel to the hinge axis.

In still another aspect, the knee orthosis comprises a breathable sleeve having attachment positions for anchoring and adjusting the medial tracking member and the inward tracking member.

In yet another aspect, the medial tracking member comprises a synthetic tube, a raised spacing member, or a raised extension member.

In still another aspect, the inward tracking member comprises an elastic, adjustable strap.

Another aspect of the invention is directed to a knee orthosis that includes an inward tracking member that operatively fits over, and provides inward pressure against, a patella having patellofemoral articular tissue; wherein the inward tracking member provides a compressive force against the patella, thereby increasing the contact surface area between the patellofemoral articular tissue and an associated femoral trochlear groove.

Another aspect of the invention is directed to an orthotic method for tracking a patella that includes applying a medial tracking member that operatively fits along a lateral side of, and provides medial traction to, a patella having patellofemoral articular tissue; and applying an inward tracking member that operatively fits over, and provides inward pressure against, the patella; wherein the inward tracking member provides a compressive force against the patella as it inwardly tracks, thereby increasing the contact surface area between the patellofemoral articular tissue and an associated femoral trochlear groove.

In another aspect, the inward pressure is applied through an intermittent and progressively increased tightening of the inward tracking member.

In still another aspect, the medial traction is applied through an intermittent and progressively increased tightening of the inward tracking member.

In yet another aspect, the medial traction applied through the intermittent and progressively increased tightening of the inward tracking member increasingly stretches lateral patellar connective tissue over time.

BRIEF DESCRIPTION OF THE DRAWINGS

In the accompanying drawings, which form a part of the specification and are to be read in conjunction therewith, and in which like reference numerals are used to indicate like parts in the various views:

FIG. 1 is front view of an attached knee orthosis, according to the present invention;

FIG. 1a is a medial-side view of the knee orthosis that has vertically disposed medial tracking attachment positions, according to the present invention;

FIG. 2a is a side view of a laterally tracking patella and a partial distal side view of an associated lateral femoral condyle that illustrates a relatively small point of contact between the patella and the lateral femoral condyle;

FIG. 2b is a frontal phantom view of a patellofemoral articulation positioned behind the medial tracking member and the inward tracking member of FIG. 1, according to the present invention;

FIG. 2c is a side view of a properly tracking patella and partial distal view of an associated femur that illustrates the relatively large surface contact area after the patella receives inward compressive force, according to the present invention;

DETAILED DESCRIPTION OF THE INVENTION

Figure 3:
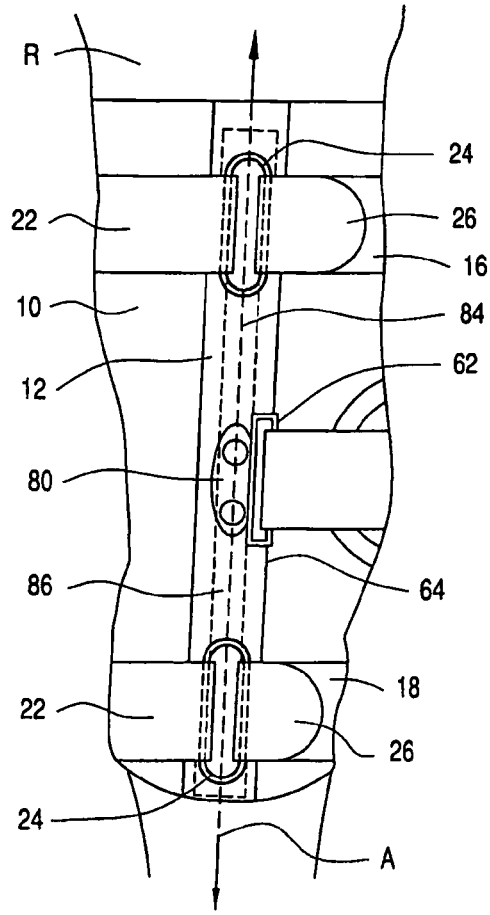
FIG. 3 is a lateral side view of the orthosis in FIG. 1.

As illustrated in the accompanying drawings and discussed in detail below, one aspect of the present invention is directed to a knee orthosis that, when used, provides continued medial traction to stretch out the lateral connective tissue of the patella. By allowing progressive, intermittent and repeated stretching of the lateral connective tissue of the patella, it increases function and speeds rehabilitation.

The knee orthosis of this aspect also directs inward pressure on the patella to increase patellofemoral surface contact area. This inward pressure accordingly reduces the damage and pain associated with patellofemoral joint disorders by evenly distributing the overall patellofemoral joint stress along a greater surface contact area, and thereby further speeds rehabilitation that would otherwise be hindered by greater pain and joint damage.

In one embodiment, the knee orthosis of the present invention provides medial and inward patellar traction. Referring to FIG. 1, knee orthosis 1 generally includes sleeve 10, medial tracking member 40, inward tracking member 60, and bicentric hinge 80.

Sleeve 10 slides into position and fits over the lower thigh, knee, and upper calf of right leg R. Sewn onto sleeve 10 are respective lateral and medial nylon webbing connection straps 12 and 14. Sleeve 10 is held in position by respective adjustable upper and lower elastic (or non-elastic, or combination thereof) attachment straps 16 and 18, which are sewn at their first ends 22 to hard plastic buckles 24. Attachment straps 16 and 18 wrap around the posterior and then the front of leg R, overlaying sleeve 10 and medial connection strap 14. Opposite ends 26 of attachment straps 16 and 18 feed through respective buckles 24, which are positioned over lateral connection strap 12, and back onto respective attachment straps 16 and 18 to adjustably tighten and secure attachment straps 16 and 18 with mating hook material 28 and loop material 29. Attachment straps 16 and 18 are held into place by locking pins 19, which protrude though grommets 21, as seen in FIG. 1a.

Sleeve 10 is made of an elastic, breathable, compressive, synthetic material such as is disclosed in U.S. Pat. No. 5,735,807, which is hereby incorporated by reference in its entirety. Appropriate materials for sleeve 10 also include, any synthetic or natural, elastic or inelastic, material suitable for use in a knee orthosis (e.g., knee orthosis 1 of FIG. 1, etc.).

Referring again to FIG. 1, medial tracking member 40 comprises 3/8 inch silicone cord 44 covered by synthetic elastic material 46 of the type described in the previously mentioned '807 patent. Suitable coverings, however, can be made from any stretchable or non-stretchable fabric. Upper and lower extension straps 48 and 50 are sewn onto both ends of cord 44 and feed through loops 52, which are sewn onto medial connection strap 14, and back onto themselves with mating hook material 54 and loop material 56 for adjustable tightening and attachment.

In an alternate embodiment, medial tracking member 40 can be further adjusted at varying angles by replacing loops 52 with upper and lower, vertically disposed attachment positions, seen in FIG. 1a, having hook material 54 or loop material 56 that corresponds to hook or loop material on extension straps 48 and 50. This feature allows extension straps 48 and 50 to be attached at various angles, in accordance with directional arrows X, in order to capture the lateral edge of the patella. Any attachment device suitable for attaching extension straps 48 and 50 can be used, however. Adjustable attachment length and angle of extension straps 48 and 50 thus serves to anchor medial tracking member 40 and allow better capturing of the lateral edge of patella P.

In fact, the amount of traction caused by medial tracking member 40 can be adjusted and readjusted by the user as needed. This feature allows the user to effectively stretch out the lateral connective tissue of the patella that is inhibiting proper movement of the patella with respect to the trochlear groove. Adjusting the traction of the patella improves the biomechanical functioning of the knee so that the knee can work more efficiently and powerfully as the quadriceps contract. The resulting better patellofemoral alignment reduces the pain in the joint by allowing a more powerful contraction of these muscles. This accordingly reduces user rehabilitation time when the orthosis is worn.

Also effective for reducing rehabilitation time is the inward force exerted by inward tracking member 60, which fits directly over the patella and holds medial tracking member 40 in place so that medial traction can be placed on patella P. Referring to FIG. 3, inward tracking member 60 comprises an elastic strap that is sewn onto ring 62, which is mounted onto hinge 80 such that its slot 64 is parallel to hinge 80's vertical axis A. Referring again to FIG. 1, end 66 overlays medial tracking member 40 and patella P, and feeds through opposing ring 68, which is mounted onto medial hinge 81, and folds back onto itself for adjustable tightening and securing with mating hook material 70 and loop material 72.

Inward tracking member 60 is made of synthetic elastic material, upon which is sewn hook 28 and loop material 29. Thus, when tightened and secured, the elasticity of inward tracking member 60 provides a consistent and continuous compressive inward force upon the patella that is substantially the same throughout a full range of flexion and extension motions. It is thus the same from about 0° to 60°, 0° to 20°, 20° to 40°, and 40° to 60° of knee flexion. Suitable materials for inward tracking member 60 include any material that can provide a continuous compressive force upon a patella that is substantially the same throughout a full range of flexion and extension motions.

Inward tracking member 60 also provides continued medial and inward tracking, throughout the rehabilitation process. Referring to FIG. 2a, patella P is tracking laterally, which induces pain in the knee joint by putting an inordinate amount of pressure on a relatively small point of contact between patella P and lateral femoral condyle C.

Referring to FIG. 2b, placing inward tracking member 60 over patella P, and tightening it applies inward pressure to better position patella P in the trochlear groove. Over the course of rehabilitation, the user follows a protocol of tightening inward tracking member 60 multiple times a day, thereby increasing both medial and inward traction on lateral connective tissues of the patella, which stretches and releases their tightness. Because these lateral connective tissues of the patella cannot be completely stretched all at once, an intermittent and progressively increased tightening is applied by readjustment of inward tracking member 60. Through such progressive tightening, inward tracking member 60 provides consistent and continued medial traction and inward pressure.

Referring to FIG. 2c, ultimately this creates more surface contact area between patella P and femur F. Application of such an inward force has been contrary to historic thinking regarding treatment of patellofemoral issues. Historically, it was thought that placing inward pressure on the patella would increase pain and wear out the articular tissue faster. Actually, the reverse is true.

Referring to FIG. 3, bicentric, hard plastic hinges 80 medial and lateral connect upper and lower upright hard nylon support members 84 and 86, which are inserted into respective lateral and medial connection straps 12 and 14. In particular, lateral hinge 80 has hard plastic ring 62, which is mounted onto lateral hinge 80 such that its slot 64 is parallel to lateral hinge 80's vertical axis A. Thus, hinge 80 serves as an anchor for inward tracking member 60. Moreover, this configuration ensures that the horizontal disposition of inward tracking member 60 remains perpendicular to, and centrally disposed with respect to, the user's knee during knee flexion and extension. Thus, suitable hinges include any unicentric and polycentric hinge that provides, or allows for, an inward tracking member 60 attachment slot that remains parallel to, and centrally disposed with respect to, the user's knee during knee flexion and extension.

Figure 4:
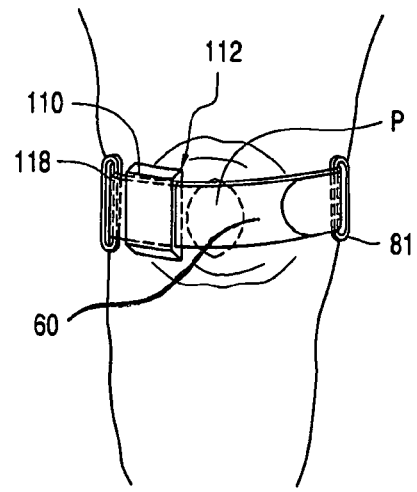
FIG. 4 is a frontal view of an attached orthosis that has an alternate medial tracking member and the inward tracking member of FIG. 1, according to the present invention.

Referring to FIG. 4, in an alternate embodiment medial tracking member 110 comprises a raised spacing member that slidably attaches to, or clips underneath, and hangs beneath inward tracking member 60. Suitable materials for the abutting edge of medial tracking member 110 include foam, silicone or any other material that has a soft edge. Medial tracking member 110 itself can be made from any material suitable to provide medial traction. Medial tracking member 110 includes slot 112, or clips (not shown), through which inward tracking member 60 feeds prior to adjustable tightening over patella P at vertical slot 114 in medial hinge 81 and being fastened in place. Medial tracking member 110 operatively abuts against lateral side of patella P and ring 118, which is mounted onto medial hinge 81, parallel to axis A (FIG. 3).

Figure 5:
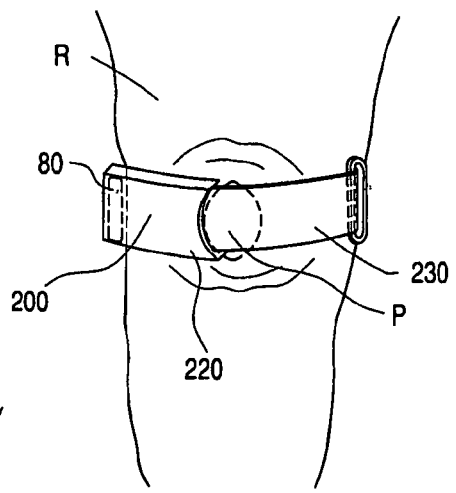
FIG. 5 is a frontal view of an attached orthosis that has another alternate medial tracking member and an alternate inward tracking member, according to the present invention.

Referring to FIG. 5, in an alternate embodiment medial tracking member 200 comprises a raised extension member that extends from hinge 80, and is drawn up against patella P by fitting elastic inward tracking member 230 over patella P. Medial tracking member 200 includes padded and raised, and specially contoured end 220, to which inward tracking member 230 attaches. Suitable materials for contoured end 220 include foam, silicone or any other material that has a soft edge. Medial tracking member 200 thus operatively abuts padded, contoured end 220 against the lateral side of patella P to provide medial traction, while inward tracking member 230 provides a continuous compressive inward force upon the patella that is substantially the same throughout a full range of flexion and extension motions.

Figure 6:
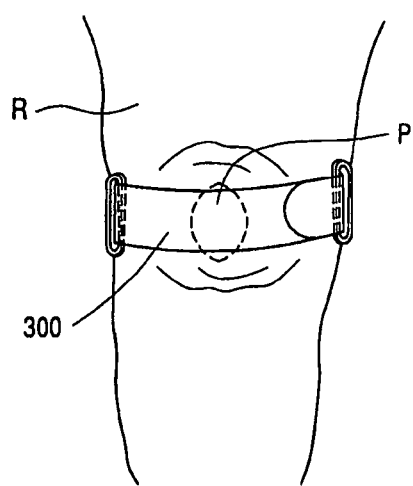
FIG. 6 is a frontal view of the inward tracking member of FIG. 1.

Referring to FIG. 6, in an alternate embodiment, the orthosis of the present invention has inward tracking member 300 but does not have a medial tracking member. Inward tracking member 300 fits over patella P and provides inward force thereon. Inward tracking member 300 is made of synthetic elastic material of the type described in the previously mentioned '807 patent. Thus, when tightened and secured, inward tracking member 300 provides a continuous compressive force upon patella P that is substantially the same throughout a full range of flexion and extension motions. Suitable materials for inward tracking member 300 include any material that can provide a continuous compressive force upon patella P that is substantially the same throughout a full range of flexion and extension motions.

Figure 7:
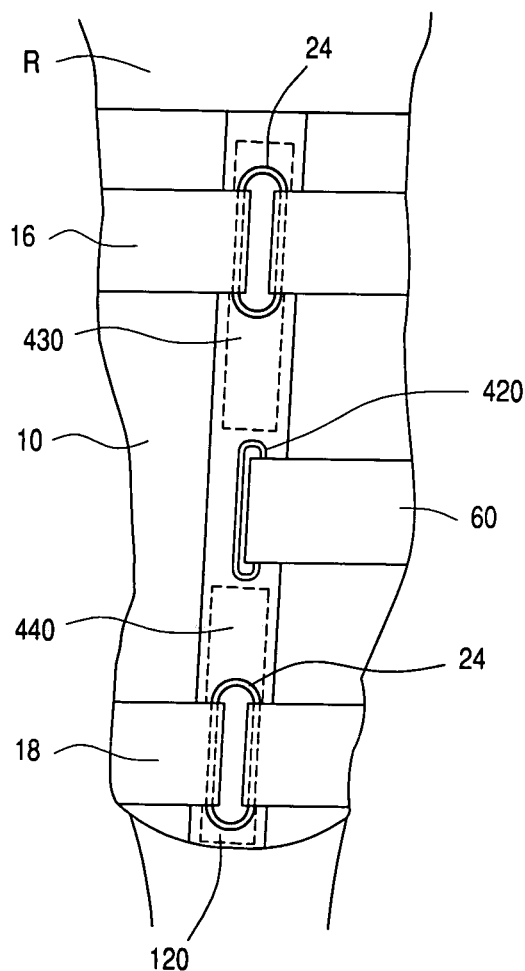
FIG. 7 is a lateral side view of a knee orthosis that has no mechanical hinge, according to the present invention.

Referring to FIG. 7, in another alternate embodiment, the orthosis of the present invention has inward tracking member 60 but does not have a mechanical hinge per se. Rather, tracking member 60 is sewn onto, and fed through, loops 420, which are sewn onto respective lateral and medial connection straps 120 and 140 (140 not shown). Hard nylon uprights 430 and 440 are respectively sewn into upper and lower portions of connection straps 120 and 140 (140 not shown).

A second aspect of the present invention is directed to an orthotic method that includes applying a medial tracking member 110 that operatively fits along a lateral side of, and provides medial traction to, a patella having patellofemoral articular tissue. The method also includes the step of applying an adjustable inward tracking member 60 that operatively fits over, and provides inward pressure onto, patella P. As a result, the inward tracking member 60 provides a compressive force against patella P as it inwardly tracks, thereby increasing the contact surface area between the patellofemoral articular tissue and an associated femoral trochlear groove.

Over the course of rehabilitation, the user follows a protocol of tightening inward tracking member 60 multiple times a day, thereby increasing both medial and inward traction on lateral connective tissues of patella P, which stretches and releases their tightness. Because these lateral connective tissues of the patella cannot be completely stretched at all at once, an intermittent and progressively increased tightening is applied by readjustment of inward tracking member 60. Through such progressive tightening, inward tracking member 60 provides consistent and continued medial and inward traction.

Other embodiments, as described above, can also be used in for this method.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments that would come within the spirit and scope of the present invention.

I claim:

1. A knee orthosis, comprising:
   a medial tracking member, including:
      a lateral element configured to be positioned along a lateral side of a patella having patellofemoral articular tissue;
      an upper element configured to be positioned above the patella, the upper element including a lateral end coupled to an upper end of the lateral element; and
      a lower element configured to be positioned below the patella, the lower element including a lateral end coupled to a lower end of the lateral element,
      the lateral element, upper element and lower element of the medial tracking member being configured to apply a selected amount of medially oriented pressure to the patella to cause the patella to track medially; and
   an inward traction member configured to:
      position the medial tracking member circumferentially around at least a portion of the patella; and
      be positioned over, and provide concentrated, medial and inward pressure and a compressive force against the patella, and to increase the contact surface area between the patellofemoral articular tissue and an associated femoral trochlear groove.

2. The knee orthosis of claim 1, wherein the inward traction member is configured to directly overlay the patella and the lateral element of the medial tracking member so that medial traction can be placed on the patella.

3. The knee orthosis of claim 1, wherein the medial tracking member is adjustable to enable selective adjustment of an amount of medial traction.

4. The knee orthosis of claim 1, wherein the inward traction member is adjustable to increase or decrease an amount of inward pressure applied to the patella.

5. The knee orthosis of claim 4, wherein the inward traction member has a plurality of intermittent inward pressure settings.

6. The knee orthosis of claim 4, wherein the inward traction member comprises an elastic, adjustable strap.

7. The knee orthosis of claim 1, wherein the inward traction member is configured to provide continuous compressive force against the patella throughout a full range of extension motion of a knee of which the patella is a part.

8. The knee orthosis of claim 7, wherein the continuous compressive force is substantially the same throughout the extension motion.

9. The knee orthosis of claim 7, wherein the continuous compressive force increases throughout the extension motion.

10. The knee orthosis of claim 1, further comprising:
a polycentric hinge having an axis that maintains a parallel position with respect to an associated knee throughout a flexion or extension motion of the knee.

11. The knee orthosis of claim 10, wherein:
the polycentric hinge is bicentric;
the inward traction member is operatively attached to the polycentric hinge; and
the inward traction member is aligned substantially perpendicular to an axis of the polycentric hinge.

12. The knee orthosis of claim 11, wherein:
the inward traction member is mounted to the polycentric hinge; or
operatively loops through a ring that is aligned parallel to the axis of the polycentric hinge.

13. The knee orthosis of claim 1, further comprising:
an elastic, breathable sleeve having attachment positions for anchoring and adjusting the medial tracking member and the inward traction member.

14. The knee orthosis of claim 1, wherein the lateral element of the medial tracking member comprises a synthetic tube that is covered with an elastic material, a raised spacing member, or a raised extension member.

15. An orthotic method for tracking a patella, comprising:
applying medial traction around a lateral side, a top and a bottom of a patella having patellofemoral articular tissue; and
applying a concentrated, inward traction against the patella to increase a contact surface area between the patellofemoral articular tissue and an associated femoral trochlear groove.

16. The method of claim 15, wherein applying the concentrated, inward traction comprises intermittently and progressively tightening an inward traction member over time.

17. The method of claim 16, wherein applying the medial traction intermittently and progressively tightening the inward traction member over time increasingly stretches lateral patellar connective tissue over time.

18. A knee orthosis, comprising:
a medial tracking member configured to at least partially surround an outer periphery of a patella having patellofemoral articular tissue and to cause the patella to track medially, the medial tracking member including:
a lateral element comprising an elongated element configured to be positioned adjacent to a lateral side of the patella, and including an upper end and a lower end;
an upper element comprising an elongated strap configured to be positioned above an upper periphery of the patella, and including a lateral end coupled to an upper end of the lateral element and a length adjustment feature configured to be positioned above the upper periphery of the patella; and
a lower element comprising an elongated strap configured to be positioned below a lower periphery of the patella, and including a lateral end coupled to the lower end of the lateral element and a length adjustment feature configured to be positioned below the lower periphery of the patella; and
an inward traction member configured to extend over the patella, between and in spaced apart relation from the upper element and the lower element of the medial tracking member, and over the lateral element of the medial tracking member to hold the medial tracking member in position relative to the patella.

19. The knee orthosis of claim 18, wherein the inward traction strap directly overlays the patella without extending to a location above or below the patella to apply a concentrated, inward compressive force to the patella and to increase a contact surface area between the patellofemoral articular tissue and an associated femoral trochlear groove.

20. The knee orthosis of claim 19, wherein at least one of the upper element and the lower element of the medial tracking member is adjustable to enable adjustment of an amount of medial traction to be applied to the patella.

21. The knee orthosis of claim 18, wherein the inward traction strap is adjustable to enable adjustment of an amount of concentrated, inward compressive force to be applied to the patella.

22. The knee orthosis of claim 21, wherein the inward traction strap provides continuous compressive force against the patella throughout a full range of extension motion of a knee associated with the patella.

23. The knee orthosis of claim 21, further comprising:
opposing lateral and medial hinges, each having a longitudinal axis that maintains a substantially parallel position with respect to the knee throughout a flexion or extension motion of the knee,
wherein a first opposing portion of the inward traction strap is operatively attached to the lateral hinge and a second opposing portion of the inward traction strap is operatively attached to the medial hinge, the inward traction strap being aligned substantially perpendicular to the longitudinal axes of the lateral and medial hinges.

24. The knee orthosis of claim 23, further comprising:
an elastic, breathable sleeve having attachment positions for anchoring and adjusting the medial tracking member and the inward traction strap.

25. An orthotic method for treating a patella, comprising:
applying a medial traction along a lateral side and at least partially around an upper periphery and a lower periphery of a patella having patellofemoral articular tissue; and
applying a concentrated, medial and inward pressure against the patella to increase a contact surface area between the patellofemoral articular tissue and an associated femoral trochlear groove while coextensively focusing the medial traction.

* * * * *